United States Patent
Uhm et al.

(10) Patent No.: US 10,386,293 B2
(45) Date of Patent: Aug. 20, 2019

(54) APPARATUS AND METHOD FOR MEASURING MOISTURE CONTENT OF COMPRESSED RECYCLED PAPER BALE

(71) Applicants: Balance Industry Co., Ltd., Seoul (KR); Industry-Academic Cooperation Foundation, Yonsei University, Seoul (KR)

(72) Inventors: Baik Yong Uhm, Seoul (KR); Won Suk Ohm, Seoul (KR); Min Ho Song, Seoul (KR); Dong Hyun Kim, Gyeonggi-do (KR)

(73) Assignees: Balance Industry Co., Ltd., Seoul (KR); Industry-Academic Cooperation Foundation, Yonsei University, Seoul (KR)

( * ) Notice: Subject to any disclaimer, the term of this patent is extended or adjusted under 35 U.S.C. 154(b) by 114 days.

(21) Appl. No.: 15/410,878

(22) Filed: Jan. 20, 2017

(65) Prior Publication Data
US 2017/0212035 A1    Jul. 27, 2017

(30) Foreign Application Priority Data
Jan. 25, 2016    (KR) .......................... 10-2016-0008946

(51) Int. Cl.
*G01N 19/10*    (2006.01)
(52) U.S. Cl.
CPC .................................. *G01N 19/10* (2013.01)
(58) Field of Classification Search
CPC ......... G01N 19/10; G01N 33/34; G01N 29/12
(Continued)

(56) References Cited

U.S. PATENT DOCUMENTS

| 4,926,691 A | * | 5/1990 | Franklin | ................ | G01H 13/00 |
| | | | | | 703/2 |
| 7,043,962 B2 | * | 5/2006 | Sakai | ..................... | B41J 11/009 |
| | | | | | 73/12.01 |

(Continued)

FOREIGN PATENT DOCUMENTS

| JP | 2001021517 A | 1/2001 |
| JP | 2009080097 A | 4/2009 |

(Continued)

OTHER PUBLICATIONS

Martinez, et al. "Vibration Testing for the Evaluation of the Effects of Moisture Content on the In-Plane Elastic Constants of Wood Used in Musical Instruments". Vibration and Structural Acoustics Analysis, 2011, pp. 21-57 (Year: 2011).*

(Continued)

*Primary Examiner* — Jonathan M Dunlap
(74) *Attorney, Agent, or Firm* — Norton Rose Fulbright US LLP

(57) ABSTRACT

The present disclosure relates to an apparatus and a method for measuring a moisture content of a compressed recycled paper bale, and the apparatus includes: an impact unit 20 which applies impact to the compressed recycled paper bale 1, and vibrates the compressed recycled paper bale 1; an acceleration sensor unit 30 which is attached to the compressed recycled paper bale 1, and detects acceleration of the compressed recycled paper bale 1 vibrated by the impact unit 20; and a control device 10 which detects a moisture content of the compressed recycled paper bale 1 by receiving a detection result from the acceleration sensor unit 30, and comparing the detection result with a vibration model of the compressed recycled paper bale.

4 Claims, 2 Drawing Sheets

(58) Field of Classification Search
USPC .................. 73/1.39, 12.01, 12.09, 73, 29.05
See application file for complete search history.

(56) References Cited

U.S. PATENT DOCUMENTS

| | | | | |
|---|---|---|---|---|
| 7,583,413 | B2* | 9/2009 | Nojiri et al. ........... | B41J 11/009 358/3.24 |
| 2004/0139783 | A1* | 7/2004 | Sakai .................... | B41J 11/009 73/12.01 |
| 2008/0011048 | A1* | 1/2008 | Kawasaki et al. ........................... | G03G 15/5029 73/12.09 |
| 2009/0007630 | A1* | 1/2009 | Kawasaki et al. ........................... | G03G 15/5029 73/12.01 |
| 2012/0073382 | A1* | 3/2012 | Spaltmann ......... | G01M 5/0025 73/788 |
| 2013/0340892 | A1* | 12/2013 | Parker ................. | G01N 29/045 144/356 |
| 2014/0069192 | A1* | 3/2014 | Bartuli .................. | G01N 29/12 73/579 |

FOREIGN PATENT DOCUMENTS

| | | |
|---|---|---|
| JP | 2010216990 A | 9/2010 |
| KR | 20080077496 | 8/2008 |

OTHER PUBLICATIONS

Song, M., *Measurement of the Moisture Content of a Waste Paper Bale Based on the Impact Resonance Test*, Doctoral Dissertation for Yonsei University Dept. of Mechanical Engineering, Jun. 19, 2015. (English abstract).

* cited by examiner

[FIG. 1]
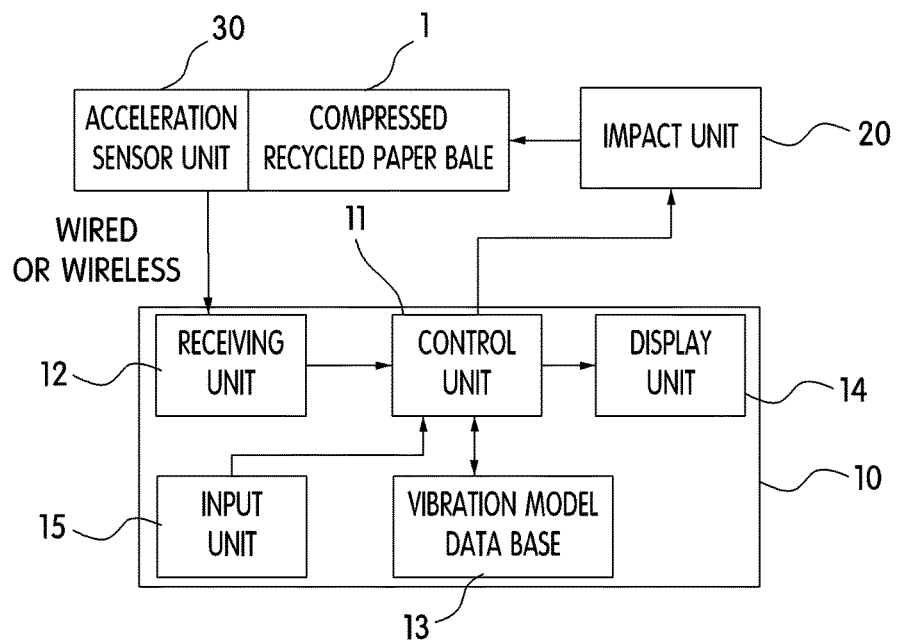

[FIG. 2]

| MOISTURE CONTENT [%] | DENSITY [kg/m³] | MODE FREQUENCY [Hz] | DAMPING RATIO |
|---|---|---|---|
| 7.93 | 303.0 | 8.090 | 0.2081 |
| 8.70 | 312.2 | 8.516 | 0.1888 |
| 9.58 | 341.9 | 11.11 | 0.1554 |
| 10.33 | 341.9 | 11.35 | 0.1519 |
| 10.62 | 209.8 | 9.462 | 0.1802 |
| 11.1 | 341.9 | 10.63 | 0.2371 |
| 15.35 | 365.2 | 12.40 | 0.1455 |
| 15.97 | 341.9 | 9.384 | 0.1860 |
| 16.06 | 365.2 | 11.69 | 0.1500 |
| 18.80 | 380.7 | 10.54 | 0.1612 |
| 22.64 | 396.3 | 11.64 | 0.1567 |
| 24.93 | 411.8 | 10.51 | 0.1722 |
| 26.68 | 357.4 | 9.540 | 0.1858 |
| 26.94 | 419.6 | 10.59 | 0.1756 |
| 27.00 | 417.1 | 11.34 | 0.1606 |
| 27.80 | 404.0 | 10.51 | 0.1721 |
| 33.30 | 349.3 | 9.29 | 0.1889 |
| 37.71 | 334.1 | 8.306 | 0.2081 |
| 38.30 | 393.9 | 8.379 | 0.1967 |

APPARATUS AND METHOD FOR MEASURING MOISTURE CONTENT OF COMPRESSED RECYCLED PAPER BALE

CROSS-REFERENCE TO RELATED APPLICATIONS

This application claims the priority of Korean Patent Application No. 10-2016-0008946 filed on Jan. 25, 2016, in the Korean Intellectual Property Office, the disclosure of which is incorporated herein by reference.

BACKGROUND

Field

The present disclosure relates to an apparatus and a method for measuring a moisture content of a compressed recycled paper bale, and more particularly, to an apparatus and a method for measuring a moisture content of a compressed recycled paper bale, which may obtain a vibration model of the compressed recycled paper bale and may measure a moisture content by using vibration of a measurement target bale based on the obtained vibration model.

Description of the Related Art

In general, recycled paper is compressed and processed in the form of a bale, and the compressed recycled paper bale is purchased by a processing company and then recycled to new paper products. However, a water feeding process of adding water into recycled paper is purposely and frequently carried out to increase a weight of the recycled paper when collecting the recycled paper, which causes problems.

If the bale has a high moisture content, the amount of paper in the bale, which may be recycled, is relatively reduced. Therefore, yields decrease and values of recycling deteriorate during a raw material process, and thus a process of accurately measuring a moisture content of the compressed recycled paper is very important to the development of the recycling industries.

A method using an electrical resistance method is most widely used in the related art as a method of measuring a moisture content of a target, and Korean Patent No. 10-1153168 (registered on May 30, 2012, entitled Multi-functional Moisture Measuring Apparatus) discloses a moisture measuring apparatus which includes a measuring unit that measures electrical resistance values between a stationary electrode and a movable electrode, and measures a moisture content of grain.

However, the electrical resistance method may be easily applied in a case in which a target, which is subjected to the moisture content measurement, has a small volume like the grain, but it is difficult to apply the electrical resistance method to a target, which has a large volume and is irregularly arranged, like the compressed recycled paper bale. Therefore, a method of measuring a moisture content of a partial region of the compressed recycled paper bale and applying the measurement result to the entire bale is used.

The method in the related art uses the result of measuring the moisture content of the partial region of the single compressed recycled paper bale as a moisture content of the entirety of the single compressed recycled paper bale, and as a result, there is a problem in that reliability deteriorates.

In addition, it is possible to more reliably measure a moisture content by measuring moisture contents of several portions of the compressed recycled paper bale and calculating an average value of the measurement results, but there is a problem in that this method requires an excessively large amount of time to measure the moisture content.

SUMMARY

An object to be achieved by the present disclosure is to provide an apparatus and a method for measuring a moisture content of a compressed recycled paper bale, which are capable of more quickly and accurately measuring a moisture content of the compressed recycled paper bale.

According to an aspect of the present disclosure, there is provided an apparatus for measuring a moisture content of a compressed recycled paper bale. The apparatus includes: an impact unit 20 which applies impact to the compressed recycled paper bale 1, and vibrates the compressed recycled paper bale 1; an acceleration sensor unit 30 which is attached to the compressed recycled paper bale 1, and detects acceleration of the compressed recycled paper bale 1 vibrated by the impact unit 20; and a control device 10 which detects a moisture content of the compressed recycled paper bale 1 by receiving a detection result from the acceleration sensor unit 30, and comparing the detection result with a vibration model of the compressed recycled paper bale.

The control device 10 may include: a receiving unit 12 which receives acceleration data detected by the acceleration sensor unit 30 in a wired or wireless manner; a vibration model data base 13 which stores the vibration model; a control unit 11 which detects the moisture content of the compressed recycled paper bale 1 by comparing the acceleration data received by the receiving unit 12 with the vibration model stored in the vibration model data base 13; and a display unit 14 which displays the detected moisture content of the compressed recycled paper bale 1.

The control device 10 may further include an input unit which receives a user's command, and inputs the user's command to the control unit 11 so as to allow the control unit 11 to operate the impact unit 20.

The control unit 11 of the control device 10 may store the acceleration data currently received by the receiving unit and the moisture content of the compressed recycled paper bale 1, which is detected based on the acceleration data, in the vibration model data base 13.

According to another aspect of the present disclosure, there is provided a method of measuring a moisture content of a compressed recycled paper bale. The method includes: step a) of obtaining a vibration model of the compressed recycled paper bale by repeatedly vibrating the compressed recycled paper bale by applying impact to the compressed recycled paper bale, and by repeatedly detecting a frequency, a damping ratio, and a moisture content of the compressed recycled paper bale; step b) of vibrating a compressed recycled paper bale 1, which is subjected to the moisture content measurement, by applying impact to the compressed recycled paper bale 1; and step c) of detecting a moisture content of the compressed recycled paper bale 1 by measuring acceleration of the compressed recycled paper bale 1, and comparing the measured acceleration data with the vibration model.

Step c) may measure acceleration of the vibrating compressed recycled paper bale 1 by attaching an acceleration sensor unit 30 to the compressed recycled paper bale 1.

The acceleration data and the moisture content, which are detected in step c), may be used as the vibration model.

According to the apparatus and the method for measuring a moisture content of a compressed recycled paper bale according to the present disclosure, it is possible to measure the moisture content of the entire compressed recycled paper bale, by obtaining a vibration model of the compressed recycled paper bale, applying predetermined impact force to the measurement target bale, measuring acceleration of the compressed recycled paper bale vibrated by the impact, and comparing the acceleration and the vibration model so as to measure a moisture content, and as a result, there is an effect of improving reliability in respect to the measurement of the moisture content.

In addition, the present disclosure may measure the moisture content by measuring acceleration obtained by applying impact to the compressed recycled paper bale, and comparing the acceleration and the vibration model, and as a result, it is possible to reduce time required for the measurement.

BRIEF DESCRIPTION OF THE DRAWINGS

The above and other aspects, features and other advantages of the present disclosure will be more clearly understood from the following detailed description taken in conjunction with the accompanying drawings, in which:

FIG. 1 is a block configuration diagram of an apparatus for measuring a moisture content of a compressed recycled paper bale according to the present disclosure; and FIG. 2 is a table illustrating an example of a vibration model of the compressed recycled paper bale.

DETAILED DESCRIPTION OF THE PREFERRED EMBODIMENT

An apparatus and a method for measuring a moisture content of a compressed recycled paper bale according to the present disclosure will be described in detail with reference to the accompanying drawings.

FIG. 1 is a block configuration diagram of an apparatus for measuring a moisture content of a compressed recycled paper bale according to an exemplary embodiment of the present disclosure.

Referring to FIG. 1, the apparatus for measuring a moisture content of a compressed recycled paper bale according to the exemplary embodiment of the present disclosure includes an impact unit 20 which applies predetermined impact force to a compressed recycled paper bale 1, an acceleration sensor unit 30 which is fixed to the compressed recycled paper bale 1, measures acceleration of the compressed recycled paper bale 1 to which the impact is applied by the impact unit 20, and transmits the acceleration, and a control device 10 which measures a moisture content by controlling an operation of the impact unit 20, receiving the acceleration of the compressed recycled paper bale 1 from the acceleration sensor unit 30, and comparing the acceleration with a vibration model of the compressed recycled paper bale.

The control device 10 includes a receiving unit 12 which receives an acceleration signal from the acceleration sensor unit 30, an input unit 15 to which a user's command may be inputted, a vibration model data base 13 which stores the vibration model of the compressed recycled paper bale 1, and a control unit 11 which measures the moisture content of the compressed recycled paper bale 1 by controlling the operation of the impact unit 20 based on the user's command inputted through the input unit 15, and comparing the acceleration signal received through the receiving unit 12 with values stored in the vibration model data base 13, and displays the measurement result on a display unit 14.

Hereinafter, a configuration and an operation of the apparatus for measuring a moisture content of a compressed recycled paper bale according to the exemplary embodiment of the present disclosure, which is configured as described above, will be described in more detail.

First, the impact unit 20 is operated by being controlled by the control device 10, and the present disclosure is not limited to a configuration of the impact unit 20 as long as the impact unit 20 is configured to apply physical impact to the compressed recycled paper bale 1.

For example, the impact unit 20 may be configured to apply force, which is generated by extending a driving shaft by using a cylinder, to the compressed recycled paper bale 1, and apply impact to the compressed recycled paper bale 1 by converting rotational force of a motor into rectilinear motion.

In this case, a portion of the impact unit 20, which comes into direct contact with the compressed recycled paper bale 1, may be made of a material such as rubber or silicone capable of performing a shock absorbing function in order to prevent damage to the compressed recycled paper bale 1, and the force, which is applied by the impact unit 20, may also be set such that impact is applied to the compressed recycled paper bale 1 to the extent that the compressed recycled paper bale 1 is not damaged.

When the impact is applied to the compressed recycled paper bale 1 by the impact unit 20, the compressed recycled paper bale 1 is vibrated. In this case, the compressed recycled paper bale 1 may be placed on a ground surface or a flat surface, or may be suspended to perform a pendulum movement even by a small amount of impact.

The acceleration sensor unit 30 is attached and installed to a part of the compressed recycled paper bale 1, and detects and transmits acceleration of the compressed recycled paper bale 1 vibrated by the impact by the impact unit 20.

The acceleration sensor unit 30 may be attached to any portion of the compressed recycled paper bale 1 except for a portion to which the impact is applied by the impact unit 20, and the acceleration sensor unit 30 transmits the measured acceleration in a wired or wireless manner.

The acceleration detected by the acceleration sensor unit 30 represents vibration of the compressed recycled paper bale 1, maximum acceleration occurs when the impact is initially applied, the acceleration decreases as time passes, and it is possible to measure the moisture content of the compressed recycled paper bale 1 by using this vibration characteristics.

A vibration frequency of the compressed recycled paper bale 1 is a value that varies depending on density, Young's modulus, and Poisson's ratio of the compressed recycled paper bale 1, and the moisture content may be measured by comparing values modelled through experiments with the currently detected acceleration information.

The modelling applies impact to samples of the compressed recycled paper bale 1 by using the impact unit 20, detects a frequency and a damping ratio of vibration caused the impact, and detects the moisture content of the compressed recycled paper bale 1 by using a moisture measuring method such as an oven-dry method.

Therefore, it is possible to obtain correlations among the frequency, the damping ratio, and the moisture of the compressed recycled paper bale 1.

The detection of the frequency of the compressed recycled paper bale 1 may be specified as a primary vibration mode, and the primary vibration mode may be expressed by the following Expression 1.

$$\omega_1^2 = C_1\left(\frac{E(1-v)}{\rho(1+v)(1-2v)}\right) + C_2\left(\frac{E}{2\rho(1+v)}\right) \quad \text{[Expression 1]}$$

Here, $\omega_1$ is a primary mode frequency, $\rho$ is density, E is Young's modulus, u is Poisson's ratio, and $C_1$ and $C_2$ are constants according to a size of the bale.

$\rho$ in Expression 1 may be expressed by the following Expression 2.

$$\rho(wc) = \frac{m_p + m_w}{V} = \frac{m_p}{V(1 - wc)} \quad \text{[Expression 2]}$$

In Expression 2, $m_p$ is mass of the paper of the compressed recycled paper bale 1, $m_w$ is mass of the moisture of the compressed recycled paper bale 1, and $w_c$ is a moisture content and may be expressed by $m_w/(m_p+m_w)$.

In addition, regarding the Young's modulus and the Poisson's ratio in Expression 1, results of previous researches may be used as it is. Research results regarding changes in Young's modulus and Poisson's ratio with respect to the moisture content of wood and paper may be applied, and the Young's modulus and the Poisson's ratio may be expressed by the following Expression 3 and the following Expression 4, respectively.

$$E(wc) = \alpha_1 \exp(-\alpha_2 wc^2) \quad \text{[Expression 3]}$$

$$v(wc) = \frac{0.5}{1 + \beta_1(-\beta_2 wc)} \quad \text{[Expression 4]}$$

Expression 3 is made by modelling the Young's modulus of the compressed recycled paper bale 1 as a Gaussian function based on the results of the previous researches, refers to the research result [J. A. Bristow and P. Kolseth, Paper Structure and Properties (New York: Dekker, 1986)] shown that hemicellulose is dominantly decomposed at room temperature and thus rigidity of paper having a high moisture content is decreased, and refers to the research result [W. J. Cousins, "Young's Modulus of Hemicellulose as Related to Moisture Content", Wood Sci. Technol. 12, (1978), 161-167.] shown that Young's modulus of hemicellulose is decreased along a bell-shaped curve in accordance with a moisture content.

$\alpha_1$ and $\alpha_2$ in Expression 3 are undetermined coefficients, and $\alpha_1$ and $\alpha_2$ are determined based on experimental values of the compressed recycled paper bale 1. $\alpha_1$ determines a size of the entire graph, and $\alpha_2$ determines a gradient of a reduction trajectory.

In addition, the Poisson's ratio expressed by Expression 4 is also a result of modelling the result of the previous research as a Sigmoid function in consideration that the Poisson's ratio according to a moisture content of wood tends to increase in accordance with the moisture content as disclosed in [W. W. Barkas, R. F. S. Hearmon and H. F. Rance Mechanical Properties of Wood and Paper (Amsterdam: N.H P&C, 1953)], and the tendency of the increase in Poisson's ratio is stopped after a predetermined point.

$\beta_1$ and $\beta_2$ in Expression 4 are undetermined coefficients, and $\beta_1$ and $\beta_2$ are determined based on experiment values. In addition, the numerator constant 0.5 is a maximum boundary value of the Poisson's ratio, and cannot be greater than the value. $\beta_1$ serves to determine an initial value when the moisture content is 0, and $\beta_2$ determines a gradient and a point in time regarding the increase in Poisson's ratio.

As described above, there is a difference between the primary vibration mode frequencies, which occur when the impact is applied to the compressed recycled paper bale 1, in accordance with the content of the moisture included in the compressed recycled paper bale 1. Therefore, the vibration model of the compressed recycled paper bale 1 may be obtained by accurately measuring the moisture content of the compressed recycled paper bale 1 with the respective frequencies, and the vibration model is stored in the vibration model data base 13.

FIG. 2 is a table illustrating an example of the vibration model stored in the vibration model data base 13.

Referring to FIG. 2, there are differences between the mode frequencies in accordance with the moisture content of the compressed recycled paper bale 1, and there are also differences between the damping ratios of the mode frequencies. By using the differences, it is possible to accurately measure the moisture content by applying impact to the compressed recycled paper bale 1, which is subjected to the actual measurement, by using the impact unit 20 so as to vibrate the compressed recycled paper bale 1, detecting vibration of the compressed recycled paper bale 1 by using the acceleration sensor unit 30, and comparing the vibration with the frequency of the vibration model stored in the vibration model data base 13.

The acceleration data detected by the acceleration sensor unit 30 is received by the receiving unit 12 of the control device 10 in a wireless or wired manner.

The control unit 11 of the control device 10 compares the acceleration data received by the receiving unit 12 with the frequency and the damping ratio of the vibration model stored in the vibration model data base 13, detects the current moisture content of the compressed recycled paper bale 1, and displays the moisture content on the display unit 14.

In addition, the detected acceleration data and the detected moisture content may be stored in the vibration model data base 13 again, and may be used, as new references, when the moisture content of the compressed recycled paper bale 1 is subsequently measured.

As described above, according to the present disclosure, a new vibration model may be obtained each time the moisture content of the compressed recycled paper bale 1 is measured, and it is possible to more accurately measure the moisture content as the vibration model data are accumulated.

It is obvious to those skilled in the art to which the present disclosure pertains that the present disclosure is not limited to the exemplary embodiment and various modifications and alterations may be made without departing from the technical spirit of the present disclosure.

What is claimed is:

1. An apparatus for measuring a moisture content of a compressed recycled paper bale, the apparatus comprising:
an impact unit which applies impact to the compressed recycled paper bale, and vibrates the compressed recycled paper bale;
an acceleration sensor unit which is attached to the compressed recycled paper bale, and detects acceleration of the compressed recycled paper bale vibrated by the impact unit; and
a control device which detects a moisture content of the compressed recycled paper bale by receiving a detection result from the acceleration sensor unit, and comparing the detection result with a vibration model of the compressed recycled paper bale.

2. The apparatus according to claim 1, wherein the control device includes:

a receiving unit which receives acceleration data detected by the acceleration sensor unit in a wired or wireless manner;

a vibration model data base which stores the vibration model;

a control unit which detects the moisture content of the compressed recycled paper bale by comparing the acceleration data received by the receiving unit with the vibration model stored in the vibration model data base; and a display unit which displays the detected moisture content of the compressed recycled paper bale.

3. The apparatus according to claim 2, wherein the control device further includes an input unit which receives a user's command, and inputs the user's command to the control unit so as to allow the control unit to operate the impact unit.

4. The apparatus according to claim 2, wherein the control unit of the control device stores the acceleration data currently received by the receiving unit and the detected moisture content of the compressed recycled paper bale, which is detected based on the acceleration data, in the vibration model data base.

\* \* \* \* \*